United States Patent [19]

Krisp et al.

[11] 4,256,599

[45] Mar. 17, 1981

[54] DENTURE CLEANSING TABLET AND PROCESS FOR MAKING

[76] Inventors: Werner Krisp, Heinestr. 9, 6940 Weinheim; Rainer Malkowski, Bahnhofstr. 4, 8204 Brannenburg; Mira Reuss, Nietzschestr. 4, 6800 Mannheim, all of Fed. Rep. of Germany

[21] Appl. No.: 26,498

[22] Filed: Apr. 3, 1979

Related U.S. Application Data

[63] Continuation of Ser. No. 825,035, Aug. 16, 1977, abandoned.

[30] Foreign Application Priority Data

Oct. 20, 1976 [DE] Fed. Rep. of Germany ....... 2647364

[51] Int. Cl.³ .......................... C11D 7/18; C11D 7/40; C11D 17/00
[52] U.S. Cl. ...................................... 252/99; 252/100; 252/102; 252/174; 424/53
[58] Field of Search ...................... 252/90, 95, 99, 100, 252/174, 135, 539, 102; 424/53, 149, 16

[56] References Cited

U.S. PATENT DOCUMENTS

| | | | |
|---|---|---|---|
| 2,498,344 | 2/1950 | Rider et al. | 252/103 |
| 3,105,792 | 10/1963 | White | 424/44 |
| 3,337,466 | 8/1967 | Puetzer et al. | 252/99 |
| 3,372,125 | 3/1968 | Hill | 252/99 |
| 3,607,759 | 9/1971 | Barth | 252/100 |
| 3,821,117 | 6/1974 | Breece et al. | 252/99 |
| 3,962,107 | 6/1976 | Levin et al. | 252/100 |
| 3,997,459 | 12/1976 | Bogie et al. | 252/99 |
| 4,062,793 | 12/1977 | SchUM/o/ del | 252/99 |

FOREIGN PATENT DOCUMENTS

| | | | |
|---|---|---|---|
| 2357720 | 3/1978 | Fed. Rep. of Germany | 252/142 |
| 962469 | 7/1964 | United Kingdom | 252/142 |

*Primary Examiner*—P. E. Willis, Jr.
*Attorney, Agent, or Firm*—George W. Rauchfuss, Jr.; Eugene O. Retter

[57] ABSTRACT

A two layered cleansing tablet for the self-acting cleansing of dentures. The layers of the tablet disintegrate at controlled rates so that denture cleansing action is made more efficient and effective compared to single layered tablet structures. The present tablet employs sulfonic acid in the tablet layer which disintegrates in a first stage cleansing step and further employs ethylene diamine tetraacetate in both tablet layers. Improved denture cleansing action is achieved even with no increase in the total amount of active agents employed in a tablet.

4 Claims, 3 Drawing Figures

DENTURE CLEANSING TABLET AND PROCESS FOR MAKING

This is a continuation, of application Ser. No. 825,035, filed Aug. 16, 1977, now abandoned.

BACKGROUND OF THE INVENTION

1. Field of the Invention

This invention lies in the field of self-acting denture cleansing tablets.

2. Prior Art

Cleansing tablets for an automatic or self-acting cleansing of dentures in an aqueous solution containing initially sodium bicarbonate functioning as a gas-forming component, sodium polyphosphates as lime bonding agents, additional organic calcium bonding agents and acid carriers, caroates as oxidizing agents, surfactants in the form of alkyl- or alkyl-aryl sulfonates (such as alkyl benzene sulfonates), and carrier agents and release (or parting) agents, are described, for example in the Austrian Letters Pat. No. 264,015. In use, such a conventional tablet is simultaneously placed in water with the dentures, or the like, which are to be cleansed, herein briefly referred to as dentures, whereupon such cleansing tablet then disintegrates accompanied by a more or less strong development of gas, so that the solvent medium is strongly agitated, and the nascent, chemically active substances attack the coating formed on the dentures. In the case of these known cleansing tablets, all the effective agents and components go into solution virtually simultaneously.

Such a simultaneous dissolution of components is disadvantageous because different components of cleansing tablets of this type; for example, the oxidizing or the oxygen-active caroates (salts of Caro's acid), on the one hand, and the reducing citric acid, on the other hand, in part work against one another, so that the overall cleansing effect of the cleansing bath is diminished. Moreover, the comparatively rapid run-off (or cycle) of this monostage cleansing process has the disadvantage that some substances, such as, for example, the oxygen-active substances, particularly the caroates, have very little effect at the beginning of the dissolution process in the cleansing bath, because the pre-conditions necessary in order for them to be effective, such as softening of the water, cracking and partial demineralization of the coating by sodium polyphosphates, or perphosphates, have not yet been adequately realized. As a consequence, it is necessary to use a larger quantity of active agents in order to achieve a specific minimal effect required for the cleansing of dentures than would actually be necessary if there were an improved chronological control of a given denture cleansing operation. However, increasing the relative quantity of active agents in a cleansing tablet results in the disadvantage that, when the tablet is dissolved, the cleansing bath becomes comparatively viscous, as a consequence of which the destruction and dissolution of the coating is again negatively affected.

Even in the case of cleansing tablets whose compositions differ only very slightly from that of the cleansing tablet according to the Austrian Letters Pat. No. 264,015, such as, for example, the denture cleansing tablet described in the Austrian Letters Pat. No. 275,044 which contains a content of persulfates, phosphates, surfactants, aromatic substances, germicides, soda, and starch which is soluble in lime water, which agents additionally include a dye, erythromysin, and chelating agents, the cleansing process still proceeds in one stage. Although, with the aid of the chelating agents provided therein, it is possible to chronologically control the oxidative bleaching operation as can be determined by the change in color, this known cleansing tablet is also subject to the fundamental shortcoming consisting in that not all the effective agents are capable of attacking the denture coating in an optimum, chronological phasing. The same remarks apply to the tablets described in the U.S. Letters Pat. No. 3,337,466 wherein, with the aid of persulfates and per-compounds, at pH-values above 7, oxygen is developed, and which tablets contain phosphates, surfactants, and chelating agents, such as nitrilotriacetic acid and ethylene diamine tetraacetate, as well as a polyethylene glycol having a molecular weight of 6.000 as the binding agent for compression of the tablets. Although, as a consequence of the pH-value provided, which is over 7, the surfactants here, as in the case of the cleansing tablet according to the Austrian Letters Pat. No. 275,044, wherein the cleansing bath has a pH-value of 9.5 to 11.5, are capable of becoming more effective than in the case of the cleansing tablet of the generic type (Austrian Letters Pat. No. 264,015), wherein acidic solutions having pH-values of 1 to 5 are employed, there still exists the fundamental disadvantage in the case of all these tablets which is that oxygen-active, that is, oxidizing substances, on the one hand, and reducing (or deoxidizing), as well as surface-active substances, on the other hand, are not capable of attacking the denture coating in an optimal fashion.

In the German Offenlegungsschrift No. 2,357,720, a cleansing effect which is improved as compared with the previously known cleansing tablets has been achieved without necessitating an increase in the quantity of conventionally employed active agents by virtue of the fact that the initially cited cleansing tablet is subdivided into two layers of different composition. In the case of the cleansing tablet according to the German Offenlegungsschrift No. 2,357,720, of the initially cited substances present in the first and second layer, the sodium bicarbonate acts as a pH-stabilizing, gas-forming (or producing) carrier. The sodium hexametaphosphate acts as a softener, while, in the German Offenlegungsschrift No. 2,357,720, citric acid, provided as an organic calcium-binding agent, has a reducing, anti-microbial effect, and, in addition, dissolves the tartar present on the dentures to be cleansed. The ethylene diamine tetraacetate provided in the first layer has a softening and demineralizing effect, whereby, in addition, a tartar-dissolving effect can be observed. The high molecular weight polyethylene glycol used acts as an anti-microbial effervescent agent. The surfactants, as a whole, have an emulsifying effect, and decompose the denture coating by virtue of their surface-activity in the case of the cleansing tablet according to German Offenlegungsschrift No. 2,357,720. The cleansing tablet according to the German Offenlegungsschrift No. 2,357,720 also exhibits an organic calcium bonding agent in the second layer, namely, sodium citrate, which has the same effect therein as the citric acid in the composition of the first layer of the cleansing tablet according to the German Offenlegungsschrift No. 2,357,720. The sodium pyrophosphate has a reducing and softening effect, and decomposes the denture coating by means of surface action. The caroates employed (that is, the salts of Caro's acid), act as oxidizing agents. In the cleansing tablet according to the German Offenlegungsschrift No. 2,357,720, a conventional sodium salt of a polycarboxylic acid, such as is described in the German Offenlegungsschrift No. 2,357,720, page 7, lines 15 and 16, is provided as a polymeric dye carrier with a surface-active cleansing effect. This sodium salt, in the form of a surfactant, likewise improves the cleansing effect. The German Offenlegungsschrift No. 2,357,720 discloses sodium dodecyl benzene sulfonate, for example, as an alkyl benzene sulfonate utilizable as a surfactant, to which fatty acid-disodium sulfosuccinates can also be added. The preferred molecular weight of the polyethylene glycol employed amounts to 20,000 in the case of the cleansing tablet according to the German Offenlegungsschrift No. 2,357,720.

The cleansing tablet according to the German Offenlegungsschrift No. 2,357,720, due to its construction from two layers each of different composition, has the following effect: If the two-layer cleansing tablet according to the German Offenlegungsschrift No. 2,357,720 is placed in water together with the denture to be cleansed, the respective layers of different composition go into solution at greatly differing respective speeds, which is of particular significance in that only the second layer of the cleansing tablet according to the German Offenlegungsschrift No. 2,357,720 contains oxygen-active substances. The active and auxiliary agents of the described type of which the cleansing tablet according to the German Offenlegungsschrift No. 2,357,720 is constructed are thus introduced into the cleansing bath in a graduated (or step-wise) manner, as a result of which there is a greatly improved cleansing action as compared with the previously known tablets. It has been observed that the first layer is dissolved in approximately one to three minutes, and that the second layer is dissolved in approximately seven to ten minutes, in a tablet embodiment wherein each of the two layers extends from the two end faces of the tablet approximately to half the height of the whole tablet. Thus, from the beginning, the two layers of the cleansing tablet according to the German Offenlegungsschrift No. 2,357,720 have the same contact surface with the solvent. The result, however, due to the different composition of the two layers is a totally different layer dissolution speed, the effect of which is that the dissolution of the first layer, and the first cleansing stage defined hereby, are already terminated in the aforementioned one to three minutes, whereas the dissolution of the second layer and the related second cleansing stage become fully active only after this time, and are terminated only in approximately eight to twelve minutes, calculated from the time of introducing the two-layer tablet into the cleansing bath. Moreover, during dissolution of the first layer, as well as during dissolution of the second layer, the pH-value is set at 6.5 to 7.0.

The cleansing tablet according to German Offenlegungsschrift No. 2,357,720 has been proven entirely successful; however, it has been shown that the intended cleansing effect, given a predetermined percentage content of respective active agents, is still not entirely satisfactory for achieving self-acting cleansing of dentures in aqueous media.

BRIEF SUMMARY OF THE INVENTION

The present invention provides a new and improved two-layered denture cleansing tablet adapted for the self acting cleansing of dentures in an aqueous solution. The tablet provides improved cleansing effect over the prior art (see, for example, the above discussed German Offenlegungsschrift No. 2,357,720). Such improvement is achieved surprisingly and unexpectedly through the incorporation of sulfamic acid into the first stage layer of the tablet and also through the incorporation of ethylene diamine tetraacetate into both layers of the tablet.

Surprisingly, the replacement of citric acid, provided in the case of the cleansing tablet according to the German Offenlegungsschrift No. 2,357,720, in the composition of the first layer, whose proportion therein amounts to 12 to 20% by weight of the composition of the first layer, by 15 to 20% by weight sulfamic acid greatly improves the cleansing properties in the first stage. Apparently, this results from the circumstance that sulfamic acid not only has stronger lime-binding (or bonding) properties than citric acid, but, in addition, also bleaches (or decolors) and cleanses strongly discolored coatings (plaques). The greatly improved effect of the inventive cleansing tablet, insofar as the latter can be attributed to the substitution of sulfamic acid for citric acid, possibly could be due to the act that $Ca_3(PO_4)$ is also dissolved in the coatings by forming calcium sulphamate ($CaSO_3NH_2$), resulting in a substantially greater coating-decomposition than in the case of the cleansing tablet according to the German Offenlegungsschrift No. 2,357,720, but there is no intent herein to be bound by theory.

The greatly improved denture coating decomposition effect of the first layer now presents the possibility of acting in an overall gentler (or "softer") manner in the second layer by omitting the relative quantity of sodium citrate provided in the second layer of the cleansing tablet according to the German Offenlegungsschrift No. 2,357,720, and, instead, admixing also with the second layer, in the manner indicated, an ethylene diaminetetraacetate additive having a softening and demineralizing as well as a tartar-dissolving effect. As a consequence, the active agents of the second layer have an improved capability of attacking the coatings which have already been strongly attacked by the first layer due to the effect of the sulfamic acid, so that fine impurities are removed through the penetration by liquid as well as auxiliary and active agents into the gaps in the coating produced by the action of the first layer.

An object of this invention is to provide a dental cleansing tablet which has an improved cleansing effect over the tablets taught by the prior art, such as represented by German Offenlegungsschrift No. 2.357,720, which improved effect is achievable without appreciably increasing the total relative percentage of active agents present in a given tablet, as taught by the prior art.

Another object is to provide a process for making such an improved tablet.

Another object is to provide an improved tablet of the class indicated which incorporates sulfamic acid and optimized amounts of ehtylene diamine tetraacetate.

Other and further objects, purposes, advantages, aims, utilities, features and the like will be apparent to those skilled in the art from a reading of the present specification taken together with the drawings.

DETAILED DESCRIPTION

Figure 1:
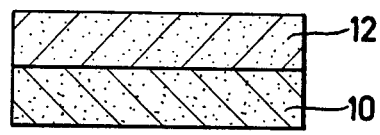
FIG. 1 is a vertical sectional view through one embodiment of a denture cleansing tablet of the present invention.

More specifically, a dental cleansing tablet of this invention for the self-acting cleansing of dentures in an aqueous medium contains sodium bicarbonate functioning as the gas-forming component, sodium polyphosphates functioning as the calcium bonding agents, additional organic calcium bonding agents and acid carriers, caroates functioning as oxidizing agents, surfactants in the form of alkyl- or alkyl-aryl sulfonates, such as alkyl benzene-sulfonates, and carriers and release (or parting) agents. Each such tablet consists of two layers of different compositions. The first tablet layer consists on a 100 weight percent dry weight basis of a homogeneous mixture of about 35 to 50% by weight of sodium bicarbonate, about 22 to 30% by weight of sodium hexametaphosphate, about 15 to 20% by weight of sulfamic acid as a lime-bonding organic acid, about 2 to 6% by weight of ethylene diamine tetraacetate, about 1 to 4% by weight of polyethylene glycol of a high-molecular weight, about 0.5 to 2% by weight of surfactants and about 0.5 to 1.5% by weight of peppermint or other aromatic (flavoring) substance. The second tablet layer consists on a 100 weight percent dry weight basis of a homogeneous mixture of about 15 to 25% by weight of sodium bicarbonate, about 8 to 15% by weight of sodium hexametaphosphate, about 10 to 15% by weight of acidic sodium pyrophosphate, about 1 to 4% by weight of a polyethylene glycol having a high molecular weight, at least about 1% by weight of a polymeric dye carrier agent exhibiting surface-active cleansing properties with a dye additive, about 3 to 6% by weight of soluble starch (amylum), about 1 to 8 weight percent of ethylene diamine tetraacetate, and about 0.5 to 1.5% by weight of peppermint or other aromatic (flavoring) substance. The total ethylene diamine tetraacetate content of both layers of any given tablet on a 100 weight percent total tablet dry weight basis ranges from about 5 to 10 weight percent.

In addition, the invention also relates to a method of manufacturing such a two layered cleansing tablet for dentures wherein each layer has a different composition. By such method, first two separate mixtures are fabricated for each layer which are subsequently mixed (or blended) together into a composition for each layer. A cleansing tablet comprising a first and a second layer is compressed from the two resulting respective compositions.

Particularly preferred embodiments of the inventive cleansing tablet will be apparent from the following description.

Thus, for example, a composition of the polymeric dye carrier consisting of one to three percent by weight of a polyvinyl pyrrolidone having a k-value of from about 24 to 27 has been proven successful. The polyvinyl pyrrolidone having a k-value of from about 24 through 27, which, in this sample embodiment, is provided in place of the sodium salt of a polycarboxylic acid provided in the case of the cleansing tablet according to German Offenlegungsschrift No. 2,357,720, is particularly well suited as a dispersion agent for the dye additive provided. In addition, this polyvinyl pyrrolidone is very readily compressible and has a very high binding capacity. In addition, there is a resulting advantage from the fact that the polyvinyl pyrrolidone is less hygroscopic than is the sodium polyacrylate preferably used in the cleansing tablet according to the German Offenlegungsschrift No. 2,357,720. The same considerations essentially apply also to other preferred embodiments of the cleansing tablet according to the invention, wherein it is possible, on the one hand, to ensure that the polymeric dye carrier consist of about 1 to 3% by weight dibasic calcium phosphate ($CaHPO_4 2H_2O$) with a heavy-metal metal content of less than about 0.1% by weight, and, on the other hand, to ensure that the polymeric dye carrier include of one to three percent by weight corn starch. For the remainder, as particularly preferred examples of the polyvinyl pyrrolidone provided herein having a k-value of about 24 to 27, it is possible to cite a substance under the trade-name of "Plasdome 25", available through the GAF Company GmbH (Germany), as well as a substance sold under the trade name of "Kollidon 25" and available from the BASF Company (Germany). As the dibasic calcium phosphorous, a substance manufactured and distributed under the trade-name of "Emcompress" by the Edward Mendell Co., Inc., New York, has been proven particularly successful. A substance obtainable under the designation "STA-RX 1500" through the HGuCBlau Company, Hamburg, Germany, is particularly suitable for use as the corn starch preparation. It is preferred to use here for a material such as a 100% corn starch, for example, a sodium glycolate of potato starch; in other words, a low substituting starch derivative of a polysaccharide.

A further preferred embodiment of the inventive cleansing tablet is distinguished by virtue of the fact that the second layer contains about 0.1 to 1% by weight silicic acid which has been manufactured by means of the hydrolysis of silicon tetrachloride in an oxyhydrogen flame. It is through this silicic acid, which is available commercially under the trade name "Aerosil," that an effective protection of the composition of the second layer against hygroscopicity is achieved.

In accordance with the invention, it is possible to further provide that the first and/or second layer contains about 0.1 to 2% by weight of sodium xylene sulfonate. Sodium xylene sulfonates of this type, such as are available under the trade name "Eltesol SX 30", or "Eltesol SX 93", from the Marchon Products Company, Ltd., Whitehaven, Great Britain, have excellent hydrotropic properties, and, in a hydrous medium, bring about an agglomeration (or deposition) of the substances which are to be dissolved, whereby the solubility of the cleansing tablet is greatly strengthened (increased). Sodium xylene sulfonates of this type also facilitate the loosening of the secondary denture coating to a great extent.

Further, it is also practical to include a cross-linked polyvinyl pyrrolidone as the additional effervescent agent, whereby the solubility is also improved, such as the material available, for example, under the trade designation "Plasdone XL" from the GAF Company, Germany GmbH, Hamburg, and such as is described in the U.S. Pat. No. 2,938,017. In aqueous systems, this polyvinyl pyrrolidone manifests a very great swelling capacity. In addition, this polyvinyl pyrrolidone is readily compressible and has good binding properties, as a consequence of which the results during tablet manufacture are excellent. Due to the large specific surface of approximately 1.0 $m^2/g$, and due to its distinctive hydrophilic character, this substance additionally has a very high capillary action, and an increased hydration capacity, as a consequence of which the cleansing properties of the inventive tablet are especially improved.

Referring to the drawings and the respective embodiments shown therein, one layer of each tablet is designated by the numeral 10, and the other layer by the numeral 12. Layer 10 is adapted to disintegrate in water before layer 12 in a first stage cleaning step or operation before layer 12 disintegrates, so that disintegration of layer 12 occurs in a second stage cleaning step or operation.

Figure 2:
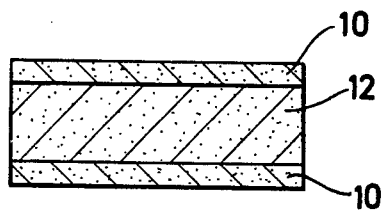
FIG. 2 is a view similar to FIG. 1, but showing an alternative embodiment of this invention.

When the cleansing tablet in accordance with the invention has the shape of a flat cylinder, such as is illustrated in the preferred embodiments shown in FIG. 2, at the two end faces of which there is respectively arranged a layer 10 consisting of the material of the first layer, and there is arranged between the layers 10 an intermediary layer 12 consisting of the material of the second layer, said intermediary layer 12 extending laterally to the cylinder covering (or enveloping) surface, the chronological separation of the two successive cleansing stages defined by the dissolution of the first and the second stage is thereby even further promoted, since the second or the intermediary layer 12 initially covered by the two first layers 10 is not completely exposed to the attack of the solvent until the first layers 10 have been decomposed.

Figure 3:
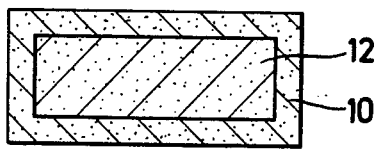
FIG. 3 is a view similar to FIG. 1, but showing a further alternative embodiment of this invention.

As shown in the FIG. 3 embodiment, the same effect occurs if the first layer 10 completely surrounds the second layer 12 in the form of a tablet-casing or envelope, in the manner of a dragee, the second layer 12 being constructed as the core of the tablet. In the first of the cleansing stages which are chronologically separated from one another, that is, in which the first layer 10 of the inventive cleansing tablet enters the cleansing bath, there is an initial softening and de-mineralization of the solvent water, whereby the denture coating is split (or cracked) open while the area of attack is being enlarged and the microorganisms present are simultaneously being combated bacteriostatically, that is, in a bactericidal fashion. The odorous and discolorant substances present in the denture coating are thereby partially absorbed and reduced while the primary coating is simultaneously de-mineralized. In referring to the primary coating on a denture, reference is herein had to the soft agglomerations (or depositions) on the denture surface, containing for example, proteinaceous substances, fats, and carbohydrates which are especially important for the formation of bacteria. It is in these agglomerations (or depositions) where the virulent bacteria of the mouth cavity flora occur; for example, staphylococci, streptococci, fibroin, spirilla, and the like.

In the second stage, which is chronologically of longer duration, the oxidizing agents, in particular, have the effect intended. The latter are able to oxidize the organic compounds of the denture coating under optimum conditions, since, due to the splitting (or cracking) open processes proceeding in the first cleansing stage, there is now present a large area of attack, and the primary coating has already been dispersed to a great extent. All the substances interfering with the action of the oxidizing agents have been substantially removed, formed into complexes, or absorbed by the action of the composition of the first layer. The primary coating is rapidly oxidized, and a secondary coating is also attacked by means of oxidation of the organic encrustations. The hard agglomerations, which are mainly of an inorganic nature, are destroyed by means of softening, emulsifying, and complex-formation. Finally, the odorous and discolorant substances are entirely absorbed and oxidized while the bacteriostatic and the bactericidal action on the remaining microorganisms is brought to a conclusion.

When different colorings of the two layers is employed whereby for examples the first layer is white, and the second layer blue, it is possible to optically follow the chronological succession of the two cleansing stages. When a tablet of this type is placed in a glass, or the like, filled with water as a cleansing bath, one can observe that, at the beginning of a cleansing operation, only the first, for example, white layer dissolves rapidly in the cleansing bath with an accompanying turbulent gas-formation without the water being colored thereby. There subsequently follows the dissolution of the second, for example, blue layer, connected with a strong but not turbulent gas-formation. The onset of the second cleansing stage is indicated by a clearly evident coloring (or tinting) of the cleansing bath brought about by the dye additive. A maximum coloration is attained when the cleansing operation has been terminated.

The inventively proposed method for the manufacture of a two-layered cleansing tablet is distinguished by virtue of the fact that, in order to produce the composition of the first layer, the indicated quantities of sodium bicarbonate, sodium hexametaphosphate, polyethylene glycol, as well as optionally sodium xylene sulfonate and cross-linked polyvinyl polypyrrolidone are mixed (or blended) together and processed into a granular substance. Then, subsequently, such a first granulated substance produced in this manner is mixed with the remaining components provided for the composition of a first layer. In order to produce the composition of the second layer, the indicated quantities of sodium bicarbonate, sodium hexametaphosphate, calcium-binding organic acid, polyethylene glycol, as well as optionally sodium xylene sulfonate and cross-linked polyvinyl polypyrrolidone are mixed (or blended) together and processed into a second granulated substance. Subsequently, the second granulated substance produced in this manner is mixed with the remaining components provided for the composition of a second layer. Finally, the individual layers of the cleansing tablet are produced from both mixtures using a tablet forming press.

It is particularly advantageous when the components provided for the first, or the second, granulated substance, respectively, are placed in a granulator (or granulating machine) heated therein to a temperature of approximately 60 to 65° C., and spun (or swirled) about at this temperature for approximately ten minutes, whereupon the thus completed first, or second, granulated substance, respectively, is cooled to approximately 25° C. Preferably, such heating of the granulated substance components proceeds by subjection to outside heated air of approximately 100 to 115° C. For the cooling process, it is preferred to provide that the cooling of the granulated substance proceed by subjection to outside air of approximately 6 to 10° C.

It has been surprisingly demonstrated that by proceeding according to this method, wherein pre-granulated substances are initially produced for each of the two layers of the inventive cleansing tablet, it is possible to achieve substantially improved cleansing-or dissolving properties than in the case of the method according to the German Offenlegungsschrift No. 2,357,720. The granulating process according to the Shynterss-effect results in stronger (or firmer) tablets which do not crumble as readily prior to use. Furthermore, the process of this invention is a simple process and guarantees an optimumized chronological staging (or phasing) of the actual dissolution of the active ingredients of the inventive cleansing tablet in a water bath.

In the sample embodiment illustrated in FIG. 1, the cleansing tablet, which essentially has the shape of a flat cylinder, is composed of two layers 10 and 12 which essentially extend or project from the end faces of the cylinder to the center plane of the cylinder.

FIG. 2 illustrates a different sample embodiment of the inventive cleansing tablet wherein a second layer 12 is covered by two layers 10 formed from the material of the first layer. The second layer 12 lies between the first layers arranged at the end faces of the flat cylinder forming the tablet. Through this form (or construction) of the tablet, the cleansing proceeds with an even clearer separation of the two stages then in the sample embodiment illustrated in FIG. 1, wherein the two-stage-nature of the second process is achieved exclusively by means of the different composition of the first and the second layer.

In the sample embodiment illustrated in FIG. 3, finally, there is a layer 12, which is adapted for the second stage of a cleansing operation, which is completely enveloped by a first layer 10, the tablet being in the form of a dragee, so that exclusively material of the first layer comes into contact with the cleansing bath during a first cleansing stage.

The ethylene diamine tetraacetate employed in the practice of this invention is a salt of ethylene diamine tetracetic acid wherein the cationic portion thereof is an alkali metal (sodium being preferred), or a mixed system of alkali metal, and alkaline earth metal (calcium being preferred), or a mixed system of alkali metal with ferric, ferrous, divalent cobalt, manganese, copper, zinc, or nickel cations.

The caroates (salts of Caro's acid) employed in the practice of this invention are alkali metal salts (sodium being preferred) of peroxymonosulfuric acid.

By the term "hardened triglyceride" reference is had to members of the class of triglyceride material being available in the Federal Republic of Germany (FRG) under trade mark BOESON VO 60.

Such a material is preferably employed in the form of a powder in the practice of this invention.

A partially cross linked polyvinyl pyrrolidone which may preferably be used in connection with the invention is available under trade mark PLASDONE XL in the U.S. and is described in U.S. Pat. No. 2,938,017.

Preferred polyethylene glycols employed in the practice of this invention have molecular weights in the range from about 18 to 24,000, though higher and lower molecular weight materials may be employed. Preferred polyethylene glycols used in the practice of the process of this invention have melting points in the range from about 60° to 65° C., though higher and lower melting materials may be employed. A particularly preferred such material has a molecular weight of about 20,000.

In general, a tablet of this invention employed in the first layer mixture the following components in the respective ranges indicated:

TABLE I

| Component | Approximate weight percentage (based on 100 weight percent total dry weight first layer) |
| --- | --- |
| 1. sodium bicarbonate | 35–50 |
| 2. sodium hexametaphosphate | 20–30 |
| 3. sulfamic acid | 15–20 |
| 4. ethylene diamine tetraacetate | 2–6 |
| 5. polyethylene glycol (mol weight ranging 18,000 to 24,000) | 1–4 |
| 6. surfactants | 0.5–1.5 |

Similarly, a tablet of this invention employs in the second layer mixture the following components in the respective ranges indicated:

TABLE II

| Component | Approximate weight percentage (based on 100 weight percent total dry weight second layer) |
| --- | --- |
| 1. sodium bicarbonate | 15–25 |
| 2. sodium hexametaphosphate | 8–15 |
| 3. ethylene diamine tetraacetate | 1–8 |
| 4. acidic sodium pyrophosphate | 10–15 |
| 5. caroates | 25–35 |
| 6. polyethylene glycol (mol weight ranging 18,000–24,000) | 1–4 |
| 7. water soluble starch | 3–6 |
| 8. water soluble cross linked polyvinyl pyrrolidone having a k-value of from about 24–27 | 0.1–2 |
| 9. dibasic calcium phosphate | 1–3 |
| 10. water soluble starch | 3–6 |
| 11. surfactants | 1–3 |

In such a tablet of this invention, the total quantity of ethylene diamine tetraacetate on a 100 weight percent total dry weight basis ranges from about 5 to 10 weight percent.

Surfactant examples for tablets of this invention are selected from the group consisting of alkali metal alkyl sulphonate, alkali metal alkyl aryl sulphonates, alkali metal xylene sulphonate, alkali metal coryl polyglycol ethers sulfosuccinates, alkali metal sulfosuccinates, and the like, preferably.

Examples of polymeric dye carriers manifesting surface active cleansing properties include polyvinyl pyrrolidone having a k-value of from about 24 to 27, sodium salts of a polycarboxylic acid, preferably sodium polyacrylate, as taught, for example, in German Offenlegungsschrift 2,357,720 at page 17, lines 15 and 16, dibasic calcium phosphate ($CaHPO_2.2H_2O$) preferably having a heavy metal content of less than about 0.1 weight percent (total weight basis), water soluble starches, and the like.

Preferably a tablet of this invention additionally contains incorporated into the second layer thereof as an emulsifying dispersion agent from 0 to about 2 weight percent of sugar fatty acid esters wherein from about 30 to 70 percent thereof comprises stearates and from about 30 to 70 weight percent thereof correspondingly comprises palmatates. Such fatty acid esters having a monoester concentration of from about 40 to 70 weight percent and, correspondingly, a di and tri ester combined combination of from about 60 to 39 weight percent (100 weight percent total fatty acid ester basis). Preferably, a tablet of this invention incorporate an anti-microbial detergent agent, such as a 4-hydroxybenzoic acid alkyl ester, or the like.

In one preferred type of tablet of this invention, the composition of a first layer 10 is preferably a homogeneous mixture and lies within the following limits (or boundaries) on a 100 weight percent dry weight basis:

| | |
|---|---|
| about 35 to 50% by weight | sodium bicarbonate, |
| about 20 to 30% by weight | sodium hexametaphosphate, |
| about 15 to 20% by weight | sulfamic acid, |
| about 2 to 6% by weight | ethylene diaminetetraacetate, |
| about 1 to 4% by weight | high-molecular-weight-polyethylene glycol having a molecular weight of 20,000, |
| about 0.1 to 2% by weight | sodium xylene sulfonate, |
| from and including 0 to about 2% by weight | bentonite |
| from and including 0 to about 1% by weight | hardened triglyceride (in powder form), |
| about 0.5 to 2% by weight | surfactants, |
| about 1 to 3% by weight | polyvinyl pyrrolidone with a k-value of 24 to 27 |
| from and including 0 to about 2% by weight | hydroxybenzoic acid alkyl ester (or another disinfectant), |
| about 0.5 to 1.5% by weight | peppermint powder |

The pH-adjustment (or setting) is such that for a given tablet the solution produced on tablet dissolution in water is about 6.5 to 7.0 during dissolution of the first layer.

Instead of peppermint powder, it is also possible to use peppermint oil, or another aromatic substance. In addition, optimally one or more further disinfectants may be added.

In contrast with the first layer 10, while composition of the second layer 12 is likewise preferably a homogenous mixture, such lies within the following limits (on a 100 weight percent dry weight basis):

| | |
|---|---|
| about 15 to 25% by weight | sodium bicarbonate, |
| about 8 to 15% by weight | sodium hexametaphosphate, |
| about 1 to 8% by weight | ethylene diamine tetraacetate, |
| about 10 to 15% by weight | acidic sodium pyrophosphate, |
| about 25 to 35% by weight | salts of Caro's acid (caroates) |
| about 1 to 4% by weight | polyethylene glycol of a high molecular weight, |
| about 0.1 to 2% by weight | cross-linked polyvinyl polypyrrolidone, |
| about 1 to 3% by weight | dibasic calcium phosphate (CaHPO$_4$ . 2 H$_2$O) with a heavy metal content of less than about 0.1% with dye additives, |
| about 3 to 6% by weight | soluble starch, |
| from and including 0 to about 2% by weight | sugar fatty acid esters consisting of 30 to 70% stearate and 70 to 30% palmitate - fatty acid component as well as with a mono-ester content of 40 to 70%, and a di- and tri-ester content of 60 to 50%, |
| from and including 0 to about 2% by weight | hydroxybenzoic acid alkyl ester, or another disinfectant, |
| from and including 0 to about 3% by weight | hardened triglyceride as lubricant (or parting compound) and smoothing agent, |
| about 0.5 to 1.5% by weight | peppermint powder, |
| about 0.1 to 1% by weight | silicic acid (produced through hydrolysis of silicon tetra-chloride in an oxyhydrogen flame), |

The pH-adjustment is such that for a given tablet the solution produced on tablet dissolution in water is about 6.5 to 7.0 during dissolution of the second layer. The total content of ethylene diamine tetraacetate of the first and the second layer together lies between about 5 and 10% by weight, in relation to the whole tablet on a 100 weight percent total dry weight basis.

In this instance also, it is possible to use peppermint oil, or another aromatic substance, instead of peppermint powder. As smoothing or wetting agents or surfactants, mixtures similar to those in the first layer may be used; for example, an alkyl benzene sulfonate and be included.

In general, a preferred process for preparing a dental cleansing tablet of the present invention involves a series of steps. In one series of steps, one dry mixes on a 100 weight percent dry total first composition weight basis about 35 to 50 weight percent sodium carbonate, from about 1 to 4 polyethylene glycol having a molecular weight as above indicated, and from about 20 to 30 weight percent sodium hexametaphosphate. Then, one simultaneously heats and tumbles such first composition. In the heating step, the first composition is heated to a temperature ranging from about 60 to 65° C. by flowing heated air therethrough. The flowing heated air has an entering temperature of from about 100 to 115° C. The tumbling of the first composition is conducted in a granulator for a time ranging from about 8 to 14 minutes. Thereafter, one admixes the resulting so-processed first composition with other components such as identified above so as to produce a first layer composition of the type identified above and adapted for use in the present invention using a conventional dry blending procedure, such as is accomplished in a tumble or double-cone drying machine. Preferably, the mixing chamber is maintained at a pressure in the range of from about 50 to 80 Torr (preferably 50 to 60 Torr) and at a temperature of from about 32 to 45° C. (more preferably 32 to 38° C.). The product mixed composition constitutes a first layer composition adapted for use in the present invention. Preferably such first layer composition has a residual moisture content of less than about 0.5 weight percent and more preferably less than about 0.25 weight percent (same basis).

Such a first layer composition and such a second layer composition are then formed into tablets of the present invention by a tableting maching.

In a second series of steps, one dry mixes on a 100 weight percent dry total second composition weight basis from about 15 to 25 weight percent sodium carbonate, from about 1 to 4 polyethylene glycol having a molecular weight as above indicated, and from about 8 to 15 weight percent sodium hexametaphosphate. Then, one simultaneously heats and tumbles such second composition. In the heating step the first composition is heated to a temperature ranging from about 60 to 65° C. by flowing heated air therethrough. The heated air has an entering temperature of from about 110 to 115° C. The tumbling of the second composition is conducted in a granulator for a time ranging from about 8 to 14 minutes. Thereafter, one admixes the resulting so-processed second composition with other components such as identified above so as to produce a second layer composition of the type adapted for use in the present invention using a conventional dry blending procedure, such as is accomplished in a tumble or double cone drying machine. Preferably the mixing chamber is maintained at a pressure in the range of from about 50 to 80 Torr (preferably 50 to 60 Torr) and at a temperature of from about 32 to 45° C. (more preferably 32 to 38° C.). The product mixed composition constitutes a second layer composition adapted for use in the present invention. Preferably such second layer composition has a residual moisture content of less than about 0.5 weight percent and more preferably less than about 0.25 weight percent (same basis).

Such a first layer composition and such a second layer composition are then formed into tablets of the present invention by a tableting machine.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

EXAMPLE 1

In order to produce the composition used for the first layer which is to effect the first cleansing stage, the first operation to be carried out consists in utilizing a conventional loading bin and elevator and feeding into a conventional mixing tank the following ingredients in succession: 132.00 kg sodium bicarbonate corresponding to a mass concentration of 44.00%, 9.00 kg polyethylene glycol having a molecular weight of 20,000, corresponding to a mass concentration of 3.00%, and 78.00 kg sodium hexametaphosphate, corresponding to a mass concentration of 26.00%. Subsequently, the mixing tank is connected to a smoothing granulating machine (here, for example, a granulator made by the firm GLATT, FRG. By supplying hot air of 100 to 155° C., the components being granulated are heated, whereby the opening for the air supply is adjusted to stage 5 through 6, and the opening for the exhaust air is adjusted (or set) to stage 2 through 3. The components to be granulated are heated under constant spinning, whereby at a component temperature of approximately 60 to 65° C. maintained for approximately ten minutes granulation takes place. At this temperature of 60 to 65° C., given the indicated duration of approximately ten minutes, the polyethylene glycol 20,000 melts without leaving any residue, as a consequence of which granulation has been fully carried out. Now maintaining the same adjustment of the air supply opening and the exhaust air opening, the granulated substance is then cooled to approximately 25° C. by supplying cooling air at a temperature of 6 to 10° C. The granulated substance is then filled into containers, for example, polyethylene bags which are then sealed against air and moisture. A constant control is maintained by taking regular test samples to ensure that the moisture content amounts to a maximum of 0.25% $H_2O$.

The granulated substance produced in this manner, a total of 219.00 kg corresponding to a mass concentration of 73.00%, is then mixed together with the remaining components of the first layer according to the method described in detail in the German Offenlegungsschrift 2,357,720 the entire contents of which are incorporated into the present specification by reference. In the case of this sample embodiment, the remaining components of the first layer are, namely, 57.00 kg of sulfamic acid, corresponding to a mass concentration of 19.00%, 1.80 kg of pulverized hardened triglyceride, corresponding to a mass concentration of 0.60%, 7.80 kg of ethylene diamine tetraacetate corresponding to a mass concentration of 2.60%, 3.00 kg of peppermint powder corresponding to a mass concentration of 1.00%, 3.00 kg of sodium benzoate corresponding to a mass concentration of 1.00%, 2.40 kg of bentonite with a high concentration of montmorrillonite, corresponding to a mass concentration of 0.80%, 60.3 weight percent, $SiO_2$, 18.5 weight percent $Al_2O_3$, 0.75 weight percent $TiO_2$, 0.25 weight percent $Fe_2O_3$, 2.2 weight percent CaO, 3.8 weight percent MgO, less than 0.1 weight percent $K_2O$ and 6.0 weight percent $Na_2O$, 1.80 kg of sodium dodecyl benzene sulfonate corresponding to a mass concentration of 0.60% and 0.90 kg of lauryl polyglycol ether sulfosuccinate corresponding to a mass concentration of 0.30%.

The composition for the second layer (second cleansing stage) is produced in a manner similar to that used for the fabrication of the composition for the first layer. Here, initially 90.00 kg of sodium bicarbonate, corresponding to a mass concentration of 18.00%, 75.00 kg of sodium hexametaphosphate, corresponding to a mass concentration of 15.00%, 35.00 kg of ethylene diamine tetraacetate, corresponding to a mass concentration of 7.00%, and 15.00 kg of polyethylene glycol having a molecular weight of 20,000 corresponding to a mass concentration of 2.00% are processed into a second granulated substance according to the granulating procedure described for the production of the first granulated substance for the first layer, as was discussed further above, Then, 129.00 kg of this second granulated substance manufactured in this manner, corresponding to a mass concentration of 43.00%, are mixed with the remaining components of the second layer; namely, 85.50 kg of caroate corresponding to a mass concentration of 28.50%, 37.50 kg of acidic disodium pyrophosphate, ($Na_2H_2P_2O_7 \cdot 6H_2O$) corresponding to a mass concentration of 12.50%, 4.50 kg of peppermint powder, corresponding to a 1.50% mass concentration, 12.00 kg of dehydrated water soluble starch, corresponding to a mass concentration of 4.00%, 4.50 kg of polyvinyl pyrrolidone with a k-value of 24 through 27, corresponding to a mass concentration of 1.50%, 0.105 kg of blue dye corresponding to a mass concentration of 0.035%, 3.00 kg of sodium benzoate, corresponding to a mass concentration of 1.00%, 21 kg of sodium bicarbonate corresponding to a mass concentration of 7.00%, 1.80 kg of sodium dodecyl benzene sulfonate corresponding to a mass concentration of 0.60%, 0.90 kg of lauryl polyglycol ether sulfosuccinate corresponding to a mass concentration of 0.30%, 1.50 kg of disodium sulfosuccinate corresponding to a mass concentration of 0.50% and 1.50 kg of alkyl aryl sulfonate corresponding to a mass concentration of 0.50%. In addition, it is noteworthy here that, in this sample embodiment, not the entire sodium bicarbonate is pre-granulated, but a further sodium bicarbonate addition occurs during mixing. This is of particular advantage for the method in accordance with the invention.

Following the production of the mixtures including drying, sieving, etc., all as described in the German Offenlegungsschrift No. 2,357,720, the two compositions are compressed into the two-layered tablet of this type shown in FIG. 1.

In the tablet of this Example, the ethylene diamine tetraacetate employed is in the form of a salt of ethylene diamine tetraacetic acid, the hardened triglyceride is BOESON VP as described above, the alkyl aryl sulfonate is the substance available under trade mark REWO-DERM S1333 from the firm REWO, FRG, the dehydrated water soluble starch is a substance available under trade mark STA-Rx 1500 from the firm STALEY, Decatur, Ill, U.S.A., the blue dye is available under trade mark COGILOR BLEU in FRG, and the polyvinyl pyrrolidone is a substance available under trade mark PLASDONE K-25 in FRG.

EXAMPLE 2

The production of the first and second layer respective compositions proceeds as in Example 1. Then, a three-layer tablet of the type shown in FIG. 2 is compressed from the two compositions for the first and second cleansing stage, wherein the two outer layers consist of the material of the first layer, whereas the inner layer is produced from the composition for the second year.

EXAMPLE 3

The production of the respective compositions for the first and second layers (first and second cleansing stages) proceeds as in Example 1. Subsequent to this, a tablet-core is first produced from the composition for the second layer, this core then being surrounded by a coating (or envelope) consisting of the material of the first layer, so as to produce a tablet of this type shown in FIG. 3.

Tablets produced in each of the preceding Examples 1 through 3 display excellent denture cleansing capability compared to prior art denture cleansing tablets when a tablet on a denture are both added, to 250 ml of distilled water, for example.

The features of the invention as disclosed in the preceding specification as well as in the following claims can be of significance individually as well as in random combination for the realization of the invention in its various embodiments.

EXAMPLE 4

The production of the first and second layer respective compositions proceeds as in Example 1, the manufacturing of the three-layer tablet of the type shown in FIG. 2 as in example 2, the fist layer, however, containing an amount of 2.0 weight percent polyvinyl pyrrolidone having the k-value specified.

What is claimed is:

1. A two-layered cleansing tablet for the self-acting cleansing of dentures in an aqueous solution comprising
    (A) a first layer comprising on a total 100 weight percent dry weight first layer basis a mixture of
        (1) from about 35 to 50 weight percent sodium bicarbonate,
        (2) from about 20 to 30 weight percent sodium hexametaphosphate,
        (3) from about 15 to 20 weight percent of sulfamic acid,
        (4) from about 2 to 6 weight percent of ethylene diamine tetraacetate,
        (5) from about 1 to 4 weight percent of polyethylene glycol having a molecular weight ranging from about 18,000 to 24,000,
        (6) from about 0.5 to 2 weight percent of surfactant,
        (7) from about 0 to 2 weight percent bentonite,
        (8) from about 0 to 1 weight percent hardened triglyceride powder,
        (9) from about 0 to 2 weight percent 4-hydroxybenzoic acid alkyl ester,
    (B) a second layer comprising on a total 100 weight percent dry weight second layer basis a mixture of
        (1) from about 15 to 25 weight percent of sodium bicarbonate,
        (2) from about 8 to 15 weight percent sodium hexametaphosphate,
        (3) from about 1 to 8 weight percent ethylene diamine tetraacetate,
        (4) from about 10 to 15 weight percent acidic sodium pyrophosphate,
        (5) from about 25 to 35 weight percent of an alkali metal salt of peroxymonosulfuric acid,
        (6) from about 1 to 4 weight percent polyethylene glycol having a molecular weight ranging from about 18,000 to 24,000,
        (7) from about 3 to 6 weight percent water soluble starch,
        (8) from about 1 to 3 weight percent of polymeric dye carrier manifesting surface active cleansing properties and selected from the the group consisting of sodium polyacrylate and a water soluble cross linked polyvinyl pyrrolidone having a k-value of from about 24 to 27,
        (9) from about 1 to 3 percent dibasic calcium phosphate having a heavy metal content of less than about 0.1 percent by weight,
        (10) from about 1 to 3 weight percent surfactant,
        (11) from about 0 to 2 weight percent of sugar fatty acid esters wherein from about 30 to 70 weight percent thereof comprises stearate and 70 to 30 weight percent thereof comprises palmitate fatty acid components on a 100 weight percent total ester basis and with a monoester content of 40 to 70 weight percent and a di-and tri-ester content of 60 to 39 weight percent on a 100 weight percent total ester basis,
        (12) from about 0 to 2 weight percent 4-hydroxybenzoic acid alkyl ester,
        (13) from about 0 to 3 weight percent hardened triglyceride
    (C) the total quantity of said ethylene diamine tetraacetate in said tablet on a 100 weight percent total dry weight basis ranging from about 5 to 10 weight percent and the pH of the solution produced on dissolution in water being from about 6.5 to 7.0 during dissolution of the first and second layers.

2. The two-layered tablet of claim 1 additionally having incorporated into said second layer thereof from about 0.1 to 1 weight percent silicic acid produced by hydrolysis of silicon tetrachloride in an oxy-hydrogen flame.

3. The two-layered tablet of claim 1 wherein said first layer contains from about 1 to 3 weight of a water soluble cross-linked polyvinyl pyrrolidone having a k-value of from about 24 to 27.

4. The two-layered tablet of claim 1 wherein said first layer contains from about 1 to 3 weight percent water soluble corn starch.

* * * * *